US010980823B2

(12) United States Patent
Feugier et al.

(10) Patent No.: US 10,980,823 B2
(45) Date of Patent: Apr. 20, 2021

(54) PERFORMANCE FOOD PRODUCT

(71) Applicant: Mars, Incorporated, McLean, VA (US)

(72) Inventors: Alexandre Feugier, Aimargues (FR); Delphine Clero, Maisons-Alfort (FR)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 16/531,349

(22) Filed: Aug. 5, 2019

(65) Prior Publication Data

US 2019/0381078 A1  Dec. 19, 2019

Related U.S. Application Data

(62) Division of application No. 14/900,021, filed as application No. PCT/EP2014/063060 on Jun. 20, 2014, now Pat. No. 10,420,783.

(30) Foreign Application Priority Data

Jun. 20, 2013 (EP) .................................... 13305838

(51) Int. Cl.
| A61K 31/7004 | (2006.01) |
| A61K 31/718 | (2006.01) |
| A61K 38/01 | (2006.01) |
| A23K 20/163 | (2016.01) |
| A23K 50/42 | (2016.01) |
| A23K 50/48 | (2016.01) |
| A23K 10/26 | (2016.01) |
| A23J 1/10 | (2006.01) |
| A61K 35/57 | (2015.01) |
| A23K 1/10 | (2006.01) |
| A23K 1/16 | (2006.01) |
| A23K 1/18 | (2006.01) |

(52) U.S. Cl.
CPC ............. *A61K 31/7004* (2013.01); *A23J 1/10* (2013.01); *A23K 1/106* (2013.01); *A23K 1/1643* (2013.01); *A23K 1/1846* (2013.01); *A23K 10/26* (2016.05); *A23K 20/163* (2016.05); *A23K 50/42* (2016.05); *A23K 50/48* (2016.05); *A61K 31/718* (2013.01); *A61K 35/57* (2013.01); *A61K 38/012* (2013.01)

(58) Field of Classification Search
CPC ........... A23J 1/10; A23K 10/26; A23K 1/106; A23K 1/1643; A23K 1/1846; A23K 20/163; A23K 50/42; A23K 50/48; A61K 31/7004; A61K 31/718; A61K 35/57; A61K 38/012
See application file for complete search history.

(56) References Cited

U.S. PATENT DOCUMENTS

| 3,642,498 A | 2/1972 | Anker |
| 3,970,614 A | 7/1976 | Goodwin |
| 4,172,073 A | 10/1979 | Allen et al. |
| 4,439,522 A | 3/1984 | Schenk |
| 4,657,762 A | 4/1987 | Mikkola et al. |
| 6,051,236 A * | 4/2000 | Portman .................. A23L 33/40 424/725 |
| 6,410,063 B1 | 6/2002 | Jewell et al. |
| 8,034,372 B2 | 10/2011 | Sidebottom et al. |
| 8,153,174 B2 | 4/2012 | Hansen |
| 9,107,867 B2 | 8/2015 | Zanghi et al. |
| 2005/0129643 A1 | 6/2005 | Lepilleur et al. |
| 2005/0176827 A1 | 8/2005 | Lee et al. |
| 2007/0141230 A1 | 6/2007 | Chenault et al. |
| 2008/0280274 A1 | 11/2008 | Freisen et al. |
| 2008/0317886 A1 | 12/2008 | Sparkman |
| 2009/0297495 A1 | 12/2009 | Kerovuo |
| 2012/0219667 A1 | 8/2012 | Kelly et al. |
| 2014/0093609 A1 | 4/2014 | Roy et al. |
| 2016/0143319 A1 | 5/2016 | Feugier |

FOREIGN PATENT DOCUMENTS

| CN | 102406064 A | 4/2012 |
| DE | 3539231 | 5/1987 |
| GB | 2112620 | 7/1983 |
| GB | 2315674 | 2/1998 |
| JP | 06046871 | 2/1994 |
| JP | H0759516 B2 | 3/1995 |
| RU | 2186498 C2 | 8/2002 |
| WO | 0195739 | 12/2001 |
| WO | 2010102362 | 9/2010 |

OTHER PUBLICATIONS

K. M. Zawadzki, Carbohydrate-protein complex increases the rate of muscle glycogen storage after exercise, J. Appl. Physiol. 72(5): 1854-1859, 1992.*
"A Balanced Diet", Waltham Book of Dog and Cat Nutrition, Ed. ATB, Edney, Chapter by A. Rainbird, pp. 57-74, Pergamon Press, Oxford, 1988.
"AAFCO Dog and Cat Food Nutrient Profiles", Association of American Feed Control Officials Incorporated, Nov. 2014, 24 pages.
"Nutrient Requirements of Dogs, National Academy Press, Washington DC (ISBN: 0-309-03496-5)", National Research Council, 1985, 7 pgs.
"Royal Canin Develops New Dog Food Formula using Feathermeal as Protein", Pet News, Jun. 5, 2013, https://www.petfoodindustry.com/articles/3687-royal-canin-develops-new-dog-food-formula-using-feathermeal-as-protein, 1 page.
Adler, et al., "In vitro pepsin digestability and amino acid composition in soluble and residual fractions of hydrolyzed chicken feathers", Poultry Science, vol. 97, No. 9, (May 23, 2018), pp. 3343-3357.

(Continued)

*Primary Examiner* — James H Alstrum-Acevedo
*Assistant Examiner* — Erinne R Dabkowski
(74) *Attorney, Agent, or Firm* — Mars, Incorporated

(57) ABSTRACT

The present invention relates to a foodstuff comprising feather hydrolysate for use in improving performance during exercise and/or improving recovery after exercise in a dog. It also relates to a method of improving the performance in a dog during exercise and/or improving recovery after exercise, the method comprising administering to a dog a foodstuff which comprises feather hydrolysate.

8 Claims, 11 Drawing Sheets

(56) References Cited

OTHER PUBLICATIONS

Figure 1:
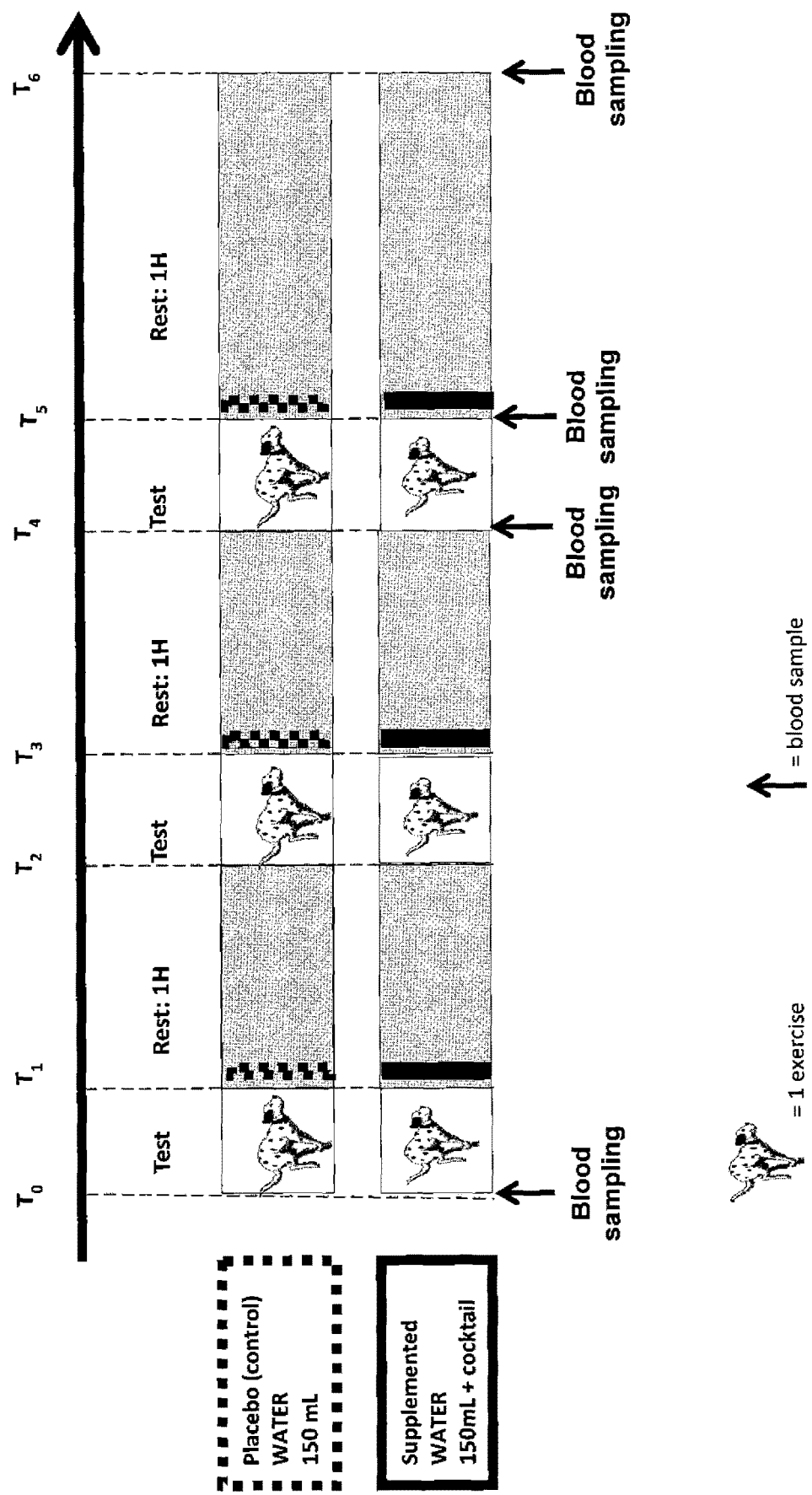

Brandelli, et al., "Biochemical Features of Microbial Keratinases and Their Production and Applications", Appl. Microbiol. Biotechnol, Feb. 2010, 85:1735-1750.

Dalev, "Utilisation of Waste Feathers from Poultry Slaughter for Production of a Protein Concentrate", Biosource Technology, 48 (Apr. 1994), 265-267.

Grazziotin, et al., "Nutritional Improvement of Feather Protein by Treatment with Microbial Keratinase", Animal Feed Sci. Terchnol., Feb. 2006, 126: 135-144.

Gupta, et al., "Bacterial Alkaline Proteases: Molecular Approaches and Industrial Applications", Appl. Microbiol. Biotechnol. (Apr. 2002), 59: 15-32.

Hamada, "Effect of amino acids and glucose on exercise-induced gut and skeletal muscle proteolysis in dogs", Metabolism, Clinical and Experimental, W.B. Saunders Co., Philadelphia, PA, US, vol. 40, No. 2, Feb. 1999, 161-166.

Lennox, "Digestion of Wool Keratin by Papain-bisulphite-urea and Related Systems", Sep. 1951, pp. 189-209.

Mintel, "Brazilian Pet Food: Complete Food for Adult Dogs", Apr. 2013, 2 pp.

Mukherjee, et al., "Biodegradation of Waste Chicken-Feathers by an Alkaline beta-Keratinase (Muartinase) Purified from a Mutant *Brevibacillus* sp. Strain AS-S10-II", International Biodeterioration & Biodegradation, vol. 65, No. 8, Sep. 6, 2011, pp. 1229-1237.

Onifade, et al., "A Review: Potentials for Biotechnological Applications of Keratin-Degrading Microorganisms and their Enzymes for Nutritional Improvement of Feathers and Other Keratins as Livestock Feed Resources", Bioresource Technology, 66 (Oct. 1998) pp. 1-11.

Ramnani, et al. "Keratinases vis-a-vis conventional proteases and feather degradation", World Journal of Microbiology and Biotechnology, May 2007, vol. 23, pp. 1537-1540.

Ramnani, et al., "Keratinolytic Potential of Bacilus Licheniformis RG1: Structural and Biochemical mechanism of Feather Degradation", Canadian Journal of Microbiology, May 2005, vol. 51, pp. 191-196.

Rebafka, et al., "Adding Value to Feathers; Goldmehl: A new potential for the Pet Food Industry", Retrieved from the Internet: URL:http://www.petfoodindustry.com/uploadedfiles/PetFoodIndustry/Articles/1003PETnovel%20feather%meal.pdf, retrieved on Sep. 29, 2014.

Tyson, "Material Data Safety Sheet—Feather Meal," May 28, 2015, 6 pages.

\* cited by examiner

PERFORMANCE FOOD PRODUCT

CROSS-REFERENCE TO RELATED APPLICATIONS

This application is a divisional of U.S. application Ser. No. 14/900,021, filed on Dec. 18, 2015 (pending), which is a 35 U.S.C. 371 of International Application No. PCT/EP2014/063060, filed on Jun. 20, 2014, which claims priority to European Patent Application No. 13305838.8 filed on Jun. 20, 2013, the entirety of each of which is hereby incorporated herein by reference for any and all purposes.

FIELD

The present invention relates to a foodstuff comprising feather hydrolysate for use in improving performance during exercise and/or improving recovery after exercise in a dog. It also relates to a method of improving the performance in a dog during exercise and/or improving recovering after exercise, the method comprising administering to a dog a foodstuff which comprises feather hydrolysate.

BACKGROUND

Dogs are commonly selected and trained to assist and/or entertain their owners. Working dogs are trained to perform tasks. Such tasks may be intense exercises performed in short durations (resistance exercise), as well as prolonged exercises which require endurance. Working dogs, such as police or army dogs, include dogs which perform rescue, search, herding or hunting. Sporting dogs are selected for their ability to perform at high levels of intensity. Sporting dogs, include dogs which race in tracks or perform agility tests.

Such working or competing dogs become tired, loose their energy and stamina and are unable to perform the next task and/or exercise.

Most commonly, high in carbohydrates products are used as the main source of fuel in energy foods for dogs performing short intense exercises.

There is a continuing need to improve performance, enhance stamina and hasten the recovery after exercise for working dogs or competing dogs to maintain a high performance level for each potential new intervention or competition run that may occur within the same day.

The present invention provides a composition that addresses this need.

The first aspect of this invention relates to a foodstuff for use in improving performance during exercise and/or improving recovery after exercise in a dog.

In particular, the foodstuff can be used for enhancing endurance and/or prolonging the stamina of the dog while exercising.

Improving performance in a dog during exercise can be enhancing the dog's performance during the exercise by allowing the dog to continue the exercise without fatigue. Improving the recovery period of a dog after an exercise can be reducing the dog's fatigue.

Enhancing endurance and prolonging stamina of a dog during exercising includes sustaining performance or boosting the dog's energy to perform tasks during exercise in particular successive exercise. Successive exercise can be repetitive exercise of short duration, optionally including maximum intensity exercises, repetitive long duration exercises or mixed endurance and resistance exercises.

Improving performance and/or improving recovery, includes reducing tissue and cellular stresses in the dog's body, for example reducing muscle damage, reducing inflammation, reducing oxidative stress and/or reducing body temperature.

It is a major interest for working dogs (search and rescue, army, etc.) to recover quickly in order to be used quickly on other missions. Some sports, including agility, contain several trials within a day. The use of the present invention after each session aids the working dog to maintain their performance level by improving recovery after each exercise.

A first aspect of the invention provides a foodstuff comprising feather hydrolysate for use in improving performance during exercise and/or improving recovery after exercise in a dog.

The foodstuff of the first aspect of the present invention has shown to be effective in improving the performance during exercise, including successive exercise and/or improving the recovery after exercise in a dog. The composition has been demonstrated to provide, inter alia, one or more of the following:

reducing muscle damage,
reducing inflammation,
reducing oxidative stress and/or
reducing body temperature.

All of the above contribute in improving performance during exercise and/or improving the recovery after exercise in a dog.

The foodstuff comprises feather hydrolysate.

Feather hydrolysate is the product produced from hydrolysing feathers, in particular poultry feathers. Feather hydrolysate usually contains at least 75% crude protein (total amino acid content) of which at least 70% are free amino acids.

Poultry industries produce a large amount of feather wastage. Feathers have a high source of keratin protein, in particular β-keratins that are composed of protein strands hydrogen-bonded into β-pleated sheets to produce tough structures. However, raw feathers are insoluble and have a low digestibility, thus the feathers are hydrolysed in order for the protein to be digestible.

The feathers (or products containing feathers) may have been hydrolysed under pressure, hydrolysed with elevated levels of heat, hydrolysed by using acid hydrolysis including using a preconditioning agent such as enzymes before the hydrolysing process begins or any combination thereof. Different processing conditions such as time of hydrolysis, pressure, temperature and moisture can affect its digestibility, solubility and bioavailability of the resulting feather hydrolysate. The resulting feather hydrolysate has specific characteristics due to the high level of hydrolysation required; in particular a high source of total amino acid (>80%), at least 70% free amino acid, 95% of molecular weight (<1000 Dalton (1 kDa)).

Feather hydrolysate includes any protein hydrolysate that has a component which is made from feathers, in particular poultry feathers. Feather hydrolysate, includes feather meal.

Preferably, feather hydrolysate is a source of low molecular weight amino acids and L-oligopeptides, for example protamine manufactured by BCF.

Feather hydrolysate can be in the form of a powder, gel or liquid. Feather hydrolysate can be mixed with a liquid to form a paste. Preferably, feather hydrolysate is in the form of a powder.

Typically, the profile of feather hydrolysate is set out in table 1 below:

TABLE 1

| Feather hydrolysate profile | % dry matter |
| --- | --- |
| Taurine | 0.01 |
| Hydroxyproline | 0.23 |
| Aspartic Acid | 5.33 |
| Threonine | 3.70 |
| Serine | 7.88 |
| Glutamic Acid | 8.13 |
| Proline | 8.41 |
| Lanthionine | 1.65 |
| Glycine | 6.25 |
| Alanine | 3.57 |
| Cysteine | 4.99 |
| Valine | 6.28 |
| Methionine | 0.57 |
| Isoleucine | 3.79 |
| Leucine | 6.59 |
| Tyrosine | 2.33 |
| Phenylalanine | 3.97 |
| Hydroxylysine | 0.01 |
| Histidine | 0.61 |
| Ornithine | 0.30 |
| Lysine | 1.79 |
| Arginine | 5.68 |
| Tryptophan | 0.47 |
| Moisture | 6 |
| Ash | 7 |
| Protein | 83 |
| Fiber | 0.31 |

The foodstuff may further comprise hydrolysed carbohydrate. Hydrolysed carbohydrate is any carbohydrate that is hydrolysed, also called a fast sugar.

In particular, hydrolysed carbohydrate can be one or more of any simple sugar, maltose, dextrose, fructose, maltodextrin or a combination thereof.

Preferably, the hydrolysed carbohydrate is maltodextrin or dextrose or combination thereof.

In particular, the hydrolysed carbohydrate is highly soluble and dispersible in cold water (temperature below 20° C.).

Maltodextrin is an oligosaccharide which is obtained from hydrolysing starch. Maltodextrin is a polysaccharide (complex) carbohydrate, which consists of repeating units of sugars such as glucose or dextrose.

Dextrose is a simple carbohydrate derived from starch but also naturally found in foods such as fruits and honey. Dextrose has the same molecular form as glucose. However, dextrose is the biologically active form.

Digestible carbohydrates are hydrolysed carbohydrates. Hydrolysed carbohydrates are easily absorbed by the body and thus function rapidly to restore glycogen in muscle after exercise.

The foodstuff of the invention is any composition which a dog may consume as part of its diet.

The foodstuff of the invention may be or may be used in combination with a complete and balanced food which provides all the recommended vitamins and minerals for the dog in questions, for example, as described in National Research Council, 1985, Nutritional Requirements for Dogs, National Academy Press, Washington D.C. (ISBN: 0-309-03496-5); or Association of American Feed Control Officials, Official Publication 1996.

It can be any foodstuff, such as dry product, semi moist product, wet food product or a liquid and includes food supplement, a snack or a treat.

The foodstuff according to the present invention encompasses any product which a pet consumes in its diet. Thus, the invention covers standard food products including liquids, as well as pet food snacks (for example, snack bars, pet chew, crunchy treat, cereal bars, snacks, biscuits and sweet products) and supplements.

The foodstuff is preferably a commercial pet food product. Such a product is preferably sold as a product for feeding to a dog.

A typical pet foodstuff contains about 20-30% crude protein and about 10-20% fat, the remainder being carbohydrate, including dietary fiber and ash. A typical wet or moist product contains (on a dry matter basis) about 40% fat, 50% protein and the remainder being fiber and ash. The foodstuff of the invention may be a dry product (with approximately 5 to approximately 15% moisture), a semi-moist product (with approximately 15 to approximately 70% moisture) or a wet product (with approximately 70 to approximately 90% moisture).

The remaining components of the foodstuff are not essential to the invention and typical standard products can be included. The combined ingredients of the foodstuff according to the invention can provide all of the recommended vitamins and minerals for the particular animal in question (a complete and balanced food).

The foodstuff can be provided as a food supplement. The food supplement can be a powder, sauce, topping, biscuit, kibble, pocket or tablet that can be administered with or without an additional foodstuff. Where the food supplement is administered with an additional foodstuff, the food supplement can be administered sequentially simultaneously or separately. The food supplement may be mixed with the foodstuff, sprinkled over the foodstuff or served separately. Alternatively, the food supplement can be added to a liquid provided for drinking such as water or milk.

The foodstuff is preferably a cooked product. It may incorporate meat or animal derived material (such as beef, chicken, turkey, lamb, fish, blood plasma, marrow bone etc. or one or more thereof). The product alternatively may be meat free (preferably including a meat substitute such as soya, maize gluten or a soya product) in order to provide a protein source. The foodstuff may contain additional protein sources such as soya protein concentrate, milk proteins, gluten etc. The foodstuff may also contain a starch source such as one or more grains (e.g. wheat, corn, rice, oats, barley etc.), or may be starch free.

Alternatively the foodstuff of the invention may be added, mixed, sprinkled onto a complete balanced diet. The diet can be dry, semi moist or wet.

In particular, the foodstuff of the invention may be a powder with a liquid or is a gel formulation. The liquid may be any liquid that a dog consumes. The amount of liquid used to dilute the mixture is dependent on the dog's palatability when consuming and can be any amount required.

The foodstuff may be a supplement. The supplement may be a liquid or in particular a powder. The supplement may be added to any other foodstuff, for example a liquid supplement may be added to any food. A powder supplement may be sprinkled on a dry, wet or semi-moist food before eating.

The foodstuff may be a composite product containing a part which is a dry food and a part which is either semi-moist or wet. In such a product, the feather hydrolysate may be in any of the different parts of the product or in only the dry, semi-moist or wet part. Any hydrolysed carbohydrate may be in any of the different parts of the product or in only the dry, semi-moist or wet part. The feather hydrolysate and any hydrolysed carbohydrate need to be in the same part or different parts of the product, e.g. the feather hydrolysate may be in a semi-moist center part and the hydrolysed carbohydrate in a dry outer shell.

The foodstuff of the first aspect of the invention may comprise feather hydrolysate at an amount ranging from about 10-50% on a dry matter basis of the foodstuff.

Preferably, the amount of feather hydrolysate can be at an amount ranging from about 15-25%, 20-35% or 30-40% on a dry matter basis.

The foodstuff of the first aspect of the invention may further comprise hydrolysed carbohydrate at an amount ranging from about 50-90% on a dry matter basis of the foodstuff.

Preferably, the amount of hydrolysed carbohydrate can be at an amount ranging from about 60-80% or 65-75% on a dry matter basis.

The foodstuff of the first aspect of the invention may be administered to a dog in a range of an amount containing from 0.1 to 1 g of feather hydrolysate per kilogram of dog.

Preferably, the amount of feather hydrolysate can be at an amount ranging from about 0.2-0.5 g, 0.3-0.6 g, 0.4-0.8 g, 0.7-1 g of feather hydrolysate per kilogram of dog or any amount of about 0.1 g, 0.2 g, 0.3 g, 0.4 g, 0.5 g, 0.6 g, 0.7 g, 0.8 g, 0.9 or 1 g of feather hydrolysate per kilogram of dog.

The foodstuff of the first aspect of the invention may be administered to a dog in a range of an amount containing from 0.5 to 4 g of hydrolysed carbohydrate per kilogram of dog.

Preferably, the amount of hydrolysed carbohydrate can be at an amount ranging from about 0.5-2 g, 1.5-3 g, 2.5-4 g or 1-3.5 g of hydrolysed carbohydrate per kilogram of dog or any amount of about 0.5 g, 1 g, 1.5 g, 2 g, 2.5 g, 3 g, 3.5 g or 4 g of hydrolysed carbohydrate per kilogram of dog.

The foodstuff of the first aspect of the invention may have any ratio of feather hydrolysate to hydrolysed carbohydrate from 5:1 to 1:10. Preferably, the ratio of feather hydrolysate to hydrolysed carbohydrate is from 3:1 to 1:5. Preferably, the ratio is 1:4.

The present invention relates, for all aspects, to a dog that is in need of improving performance during exercise and/or improving recovery after exercise.

The second aspect of this invention provides a method for improving performance during exercise and/or improving recovery after exercise. In particular, the method comprises administering to a dog a foodstuff which comprises feather hydrolysate (the foodstuff of the first aspect of the invention).

Further, the method is preferably administered to a dog, in particular a working dog after exercise to improve performance of the next exercise. Reducing muscular and cellular stresses improves the performance in the next exercise.

The foodstuff of the first aspect of the invention can be administered before or after exercise. The foodstuff may be administered 10 minutes, 20 minutes, 30 minutes, 45 minutes, 1 hour, 1.5 hours or 2 hours before or after exercise or immediately after the dog stops to rest after exercising, within 10 minutes, 20 minutes, 30 minutes, 45 minutes or an hour after exercise.

The foodstuff may be administered in a dietary regime in accordance with the usual dietary regime of the dog. The foodstuff may comprise 100% of the diet of the companion animal or a lesser proportion, depending on the level required. The foodstuff can be administered by the animal's owner or trainer. The foodstuff may be available at any outlet selling pet food products or may be available from a veterinarian. The foodstuff may be as described above according to the first aspect of the invention.

As used herein, the term "administration" also includes feeding or any other method of oral administration.

The foodstuff of the second aspect is as described for the first aspect of the invention (above).

Preferred features of the first aspect of the invention apply as for the second aspect of the invention mutatis mutandis.

In a third aspect of the invention there is provided a foodstuff comprising 10-50% of feather hydrolysate on a dry matter basis.

Preferred features of the first and second aspect of the invention apply as for the third aspect of the invention mutatis mutandis.

Preferably, the amount of feather hydrolysate can be an amount ranging from about 15-25%, 20-35% or 30-40% on a dry matter basis.

The foodstuff according to the third aspect of the invention may further comprise hydrolysed carbohydrate.

The foodstuff may further comprise hydrolysed carbohydrate at an amount ranging from about 50-90% on a dry matter basis of the foodstuff.

Preferably, the amount of hydrolysed carbohydrate can be at an amount ranging from about 60-80% or 65-75% on a dry matter basis.

The foodstuff of the third aspect of the invention may have any ratio of feather hydrolysate to hydrolysed carbohydrate from 5:1 to 1:10. Preferably, the ratio of feather hydrolysate to hydrolysed carbohydrate is from 3:1 to 1:5. Preferably, the ratio is 1:4.

The present invention also relates to a method of enhancing endurance and prolonging stamina of a dog during exercising and includes sustaining performance or boosting the dog's energy to perform tasks during exercise, in particular successive exercise.

The present invention also relates to a method of improving performance and/or improving recovery, and can include reducing tissue and cellular stresses in the dog's body, for example reducing muscle damage, reducing inflammation, reducing oxidative stress and/or reducing body temperature.

The present description includes a method for preparing the foodstuff of the invention.

The foodstuff can be made according to any method known in the art, for example as described in Waltham Book of Dog and Cat Nutrition, Ed. ATB Edney, Chapter by A. Rainbird, entitled "A Balanced Diet" in pages 57 to 74 Pergamon Press Oxford.

For example, a process for the manufacture of a foodstuff as defined herein comprises mixing together ingredients with the composition comprising feather hydrolysate and forming a foodstuff, in particular a pet foodstuff. Heating/cooking may be applied to any one or more of the ingredients prior to, during or following the mixing.

The feather hydrolysate and/or hydrolysed carbohydrate can be sprayed onto the foodstuff, mixed in with the foodstuff or incorporated into the foodstuff in a matrix. Methods of inclusion of the feather hydrolysate and/or hydrolysed carbohydrate composition are known in the art.

The invention will now be further described by way of reference to the following Examples and Figures, which are provided for the purpose of illustration only and are not to be construed as being limiting on the invention.

FIG. 1: shows a schematic diagram cross over design (n=10) of the design of the trial. The figure shows the stages of exercise ($T_0$-$T_1$, $T_2$-$T_3$ and $T_4$-$T_5$) stages of rest ($T_1$-$T_2$, $T_3$-$T_4$ and $T_5$-$T_6$), time of blood sampling ($T_0$, $T_4$, $T_5$ and $T_6$) and time of supplementation ($T_1$, $T_3$ and $T_5$). One exercise consists of 5 intensive sprints (100 m), 20 min of endurance at 20 km/h and 5 intensive sprints (100 m). Each dog is its own control (C) 2 weeks later when the dog repeats the same exercise and is supplemented with the foodstuff of the invention (S).

Figure 2A:
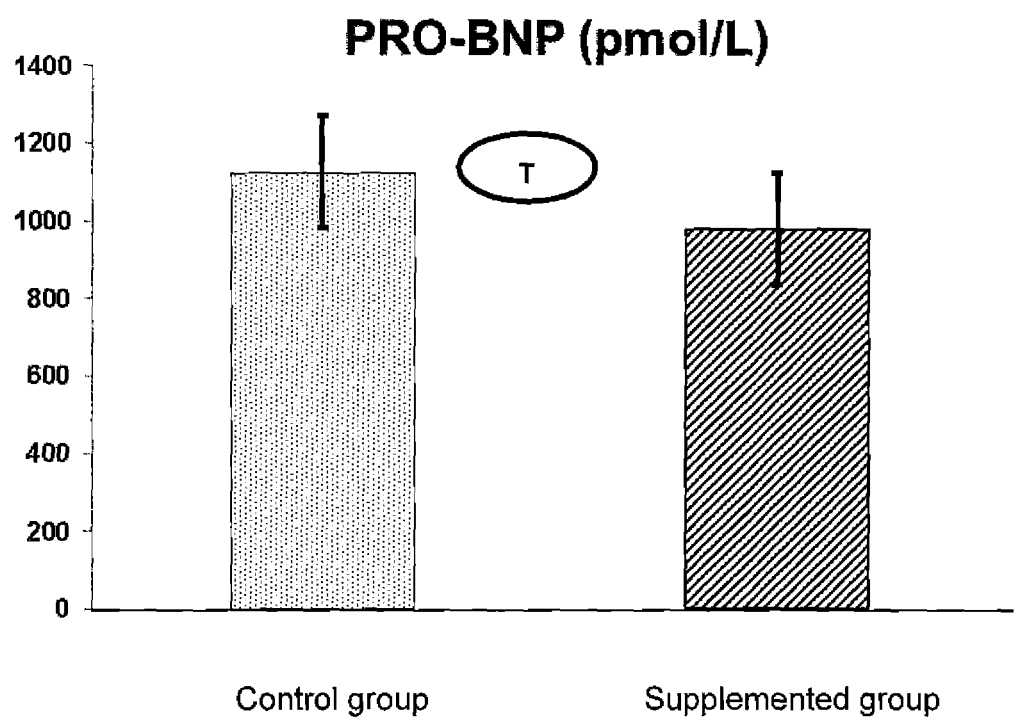
Figure 2B:
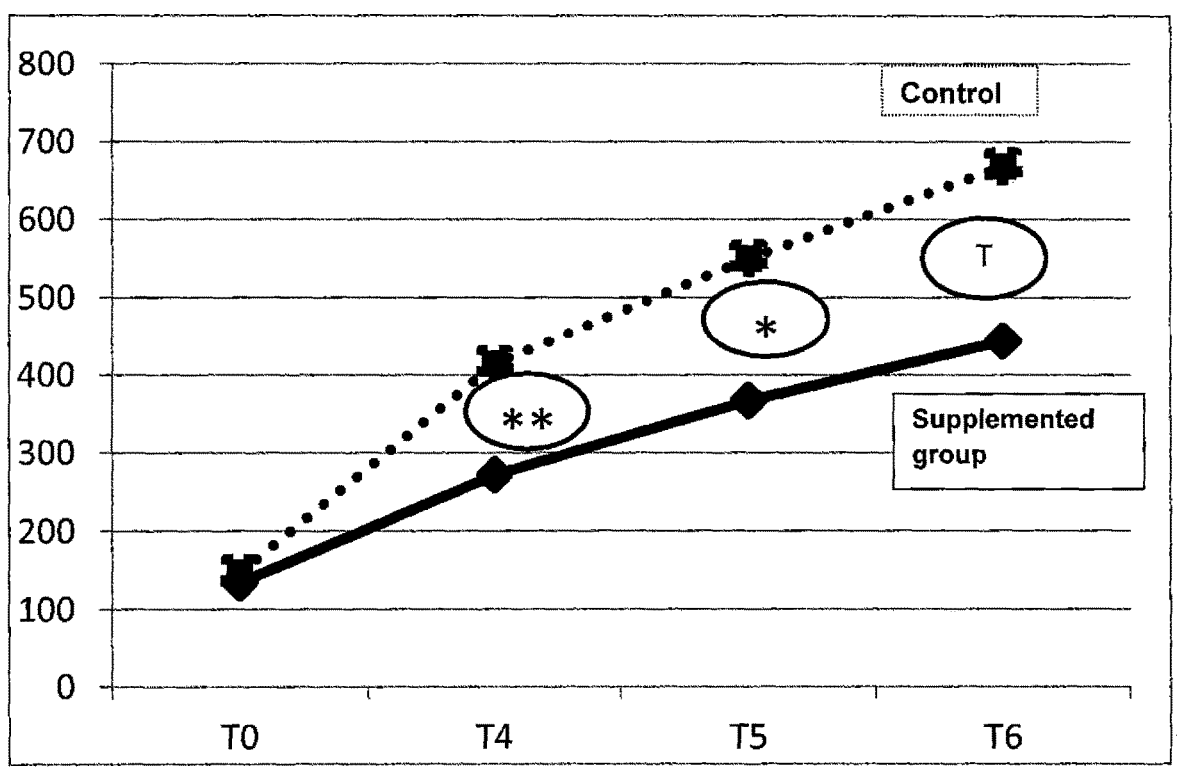

FIG. 2: shows the results obtained when assessing muscle damage. FIG. 2a shows the results obtained when assessing Pro BNP. FIG. 2b shows the results obtained when assessing creatine kinase.

FIG. 3: shows the results obtained when assessing inflammation. FIG. 3a shows the results obtained when assessing C Reactive protein (CRP). In FIG. 3b, 3c, 3d, 3e, the letters in lower case are used to assess the effect of check point (time) for the control group (within group comparison). Upper case letters are used to assess the effect of check point (time) for the supplemented group (between group comparison). Different letters show significant difference at 5%.

Figure 3A:
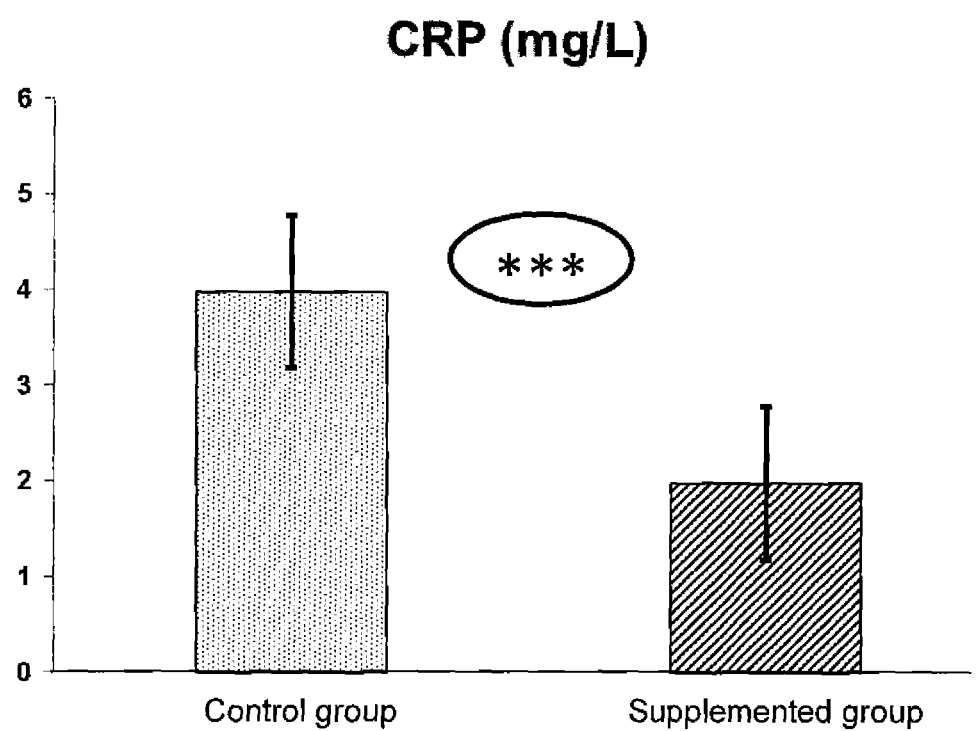
Figure 3B:
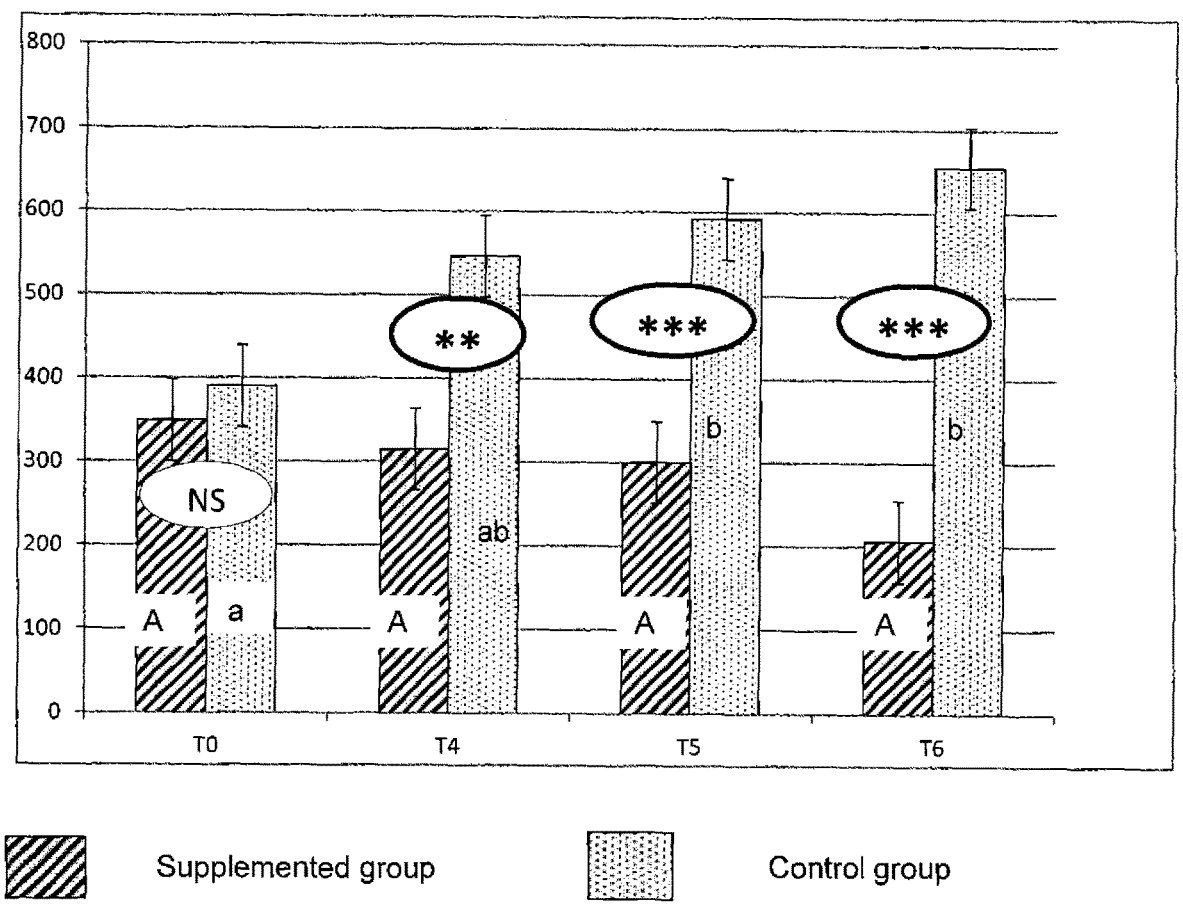
Figure 3C:
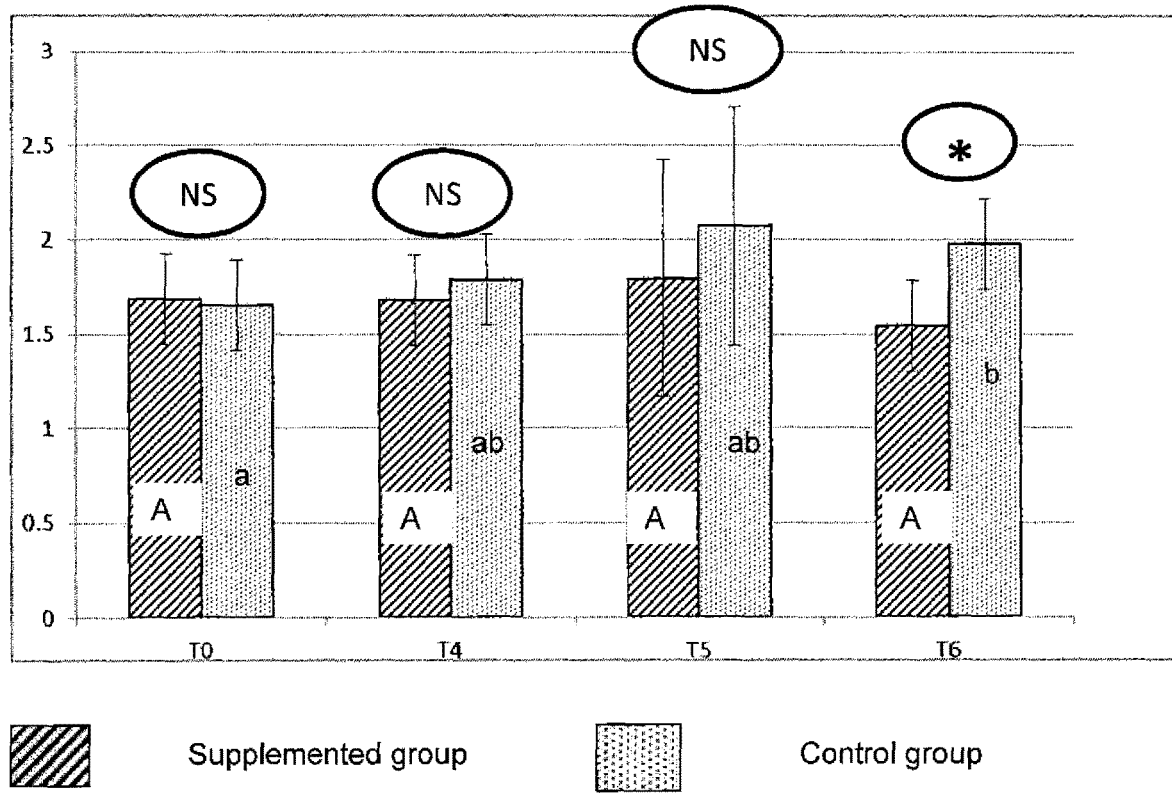
Figure 3D:
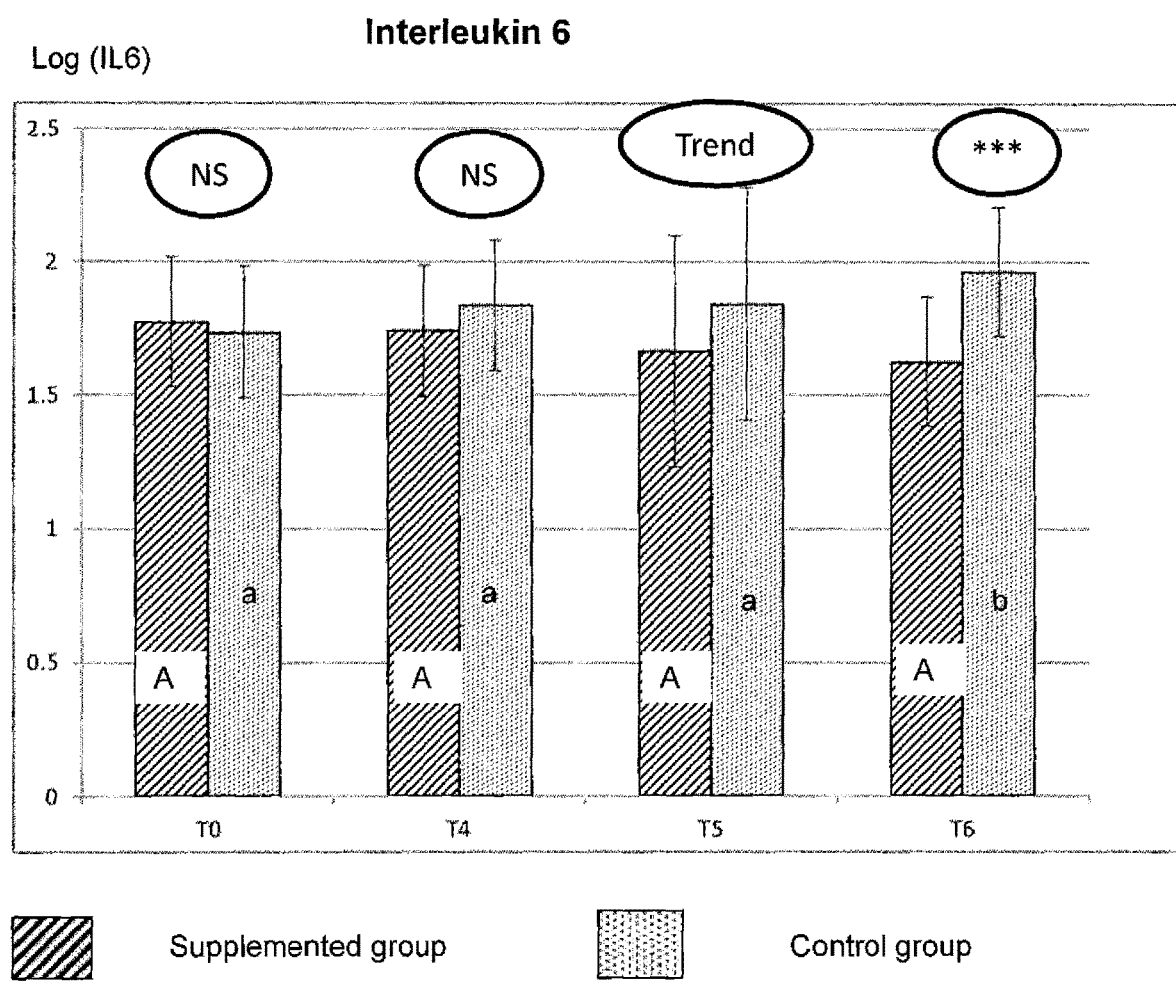
Figure 3E:
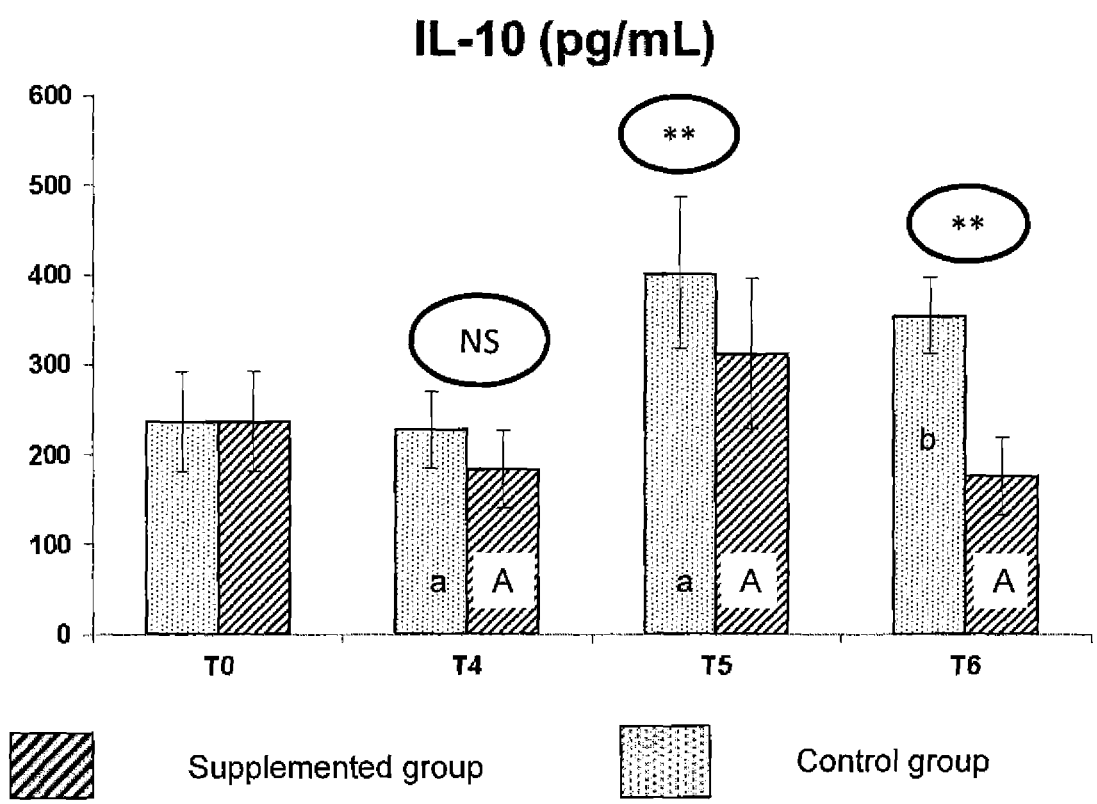

FIG. 3b shows the results obtained when assessing Myeloperoxidase (MPO). FIG. 3c shows the results obtained when assessing TNFα. FIG. 3d shows the results obtained when assessing interleukin 6 (IL6). FIG. 3e shows the results obtained when assessing interleukin 10 (IL10).

Figure 4A:
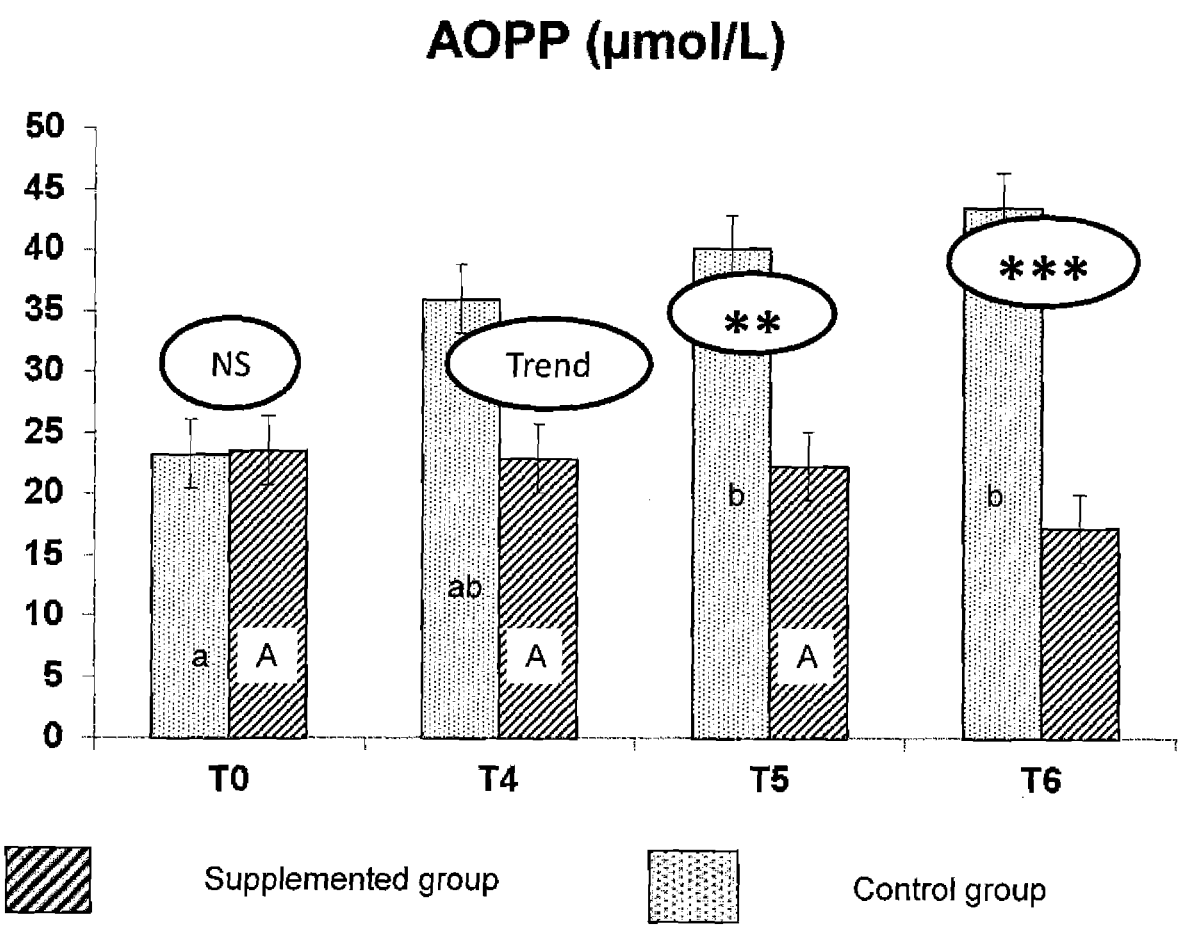
Figure 4B:
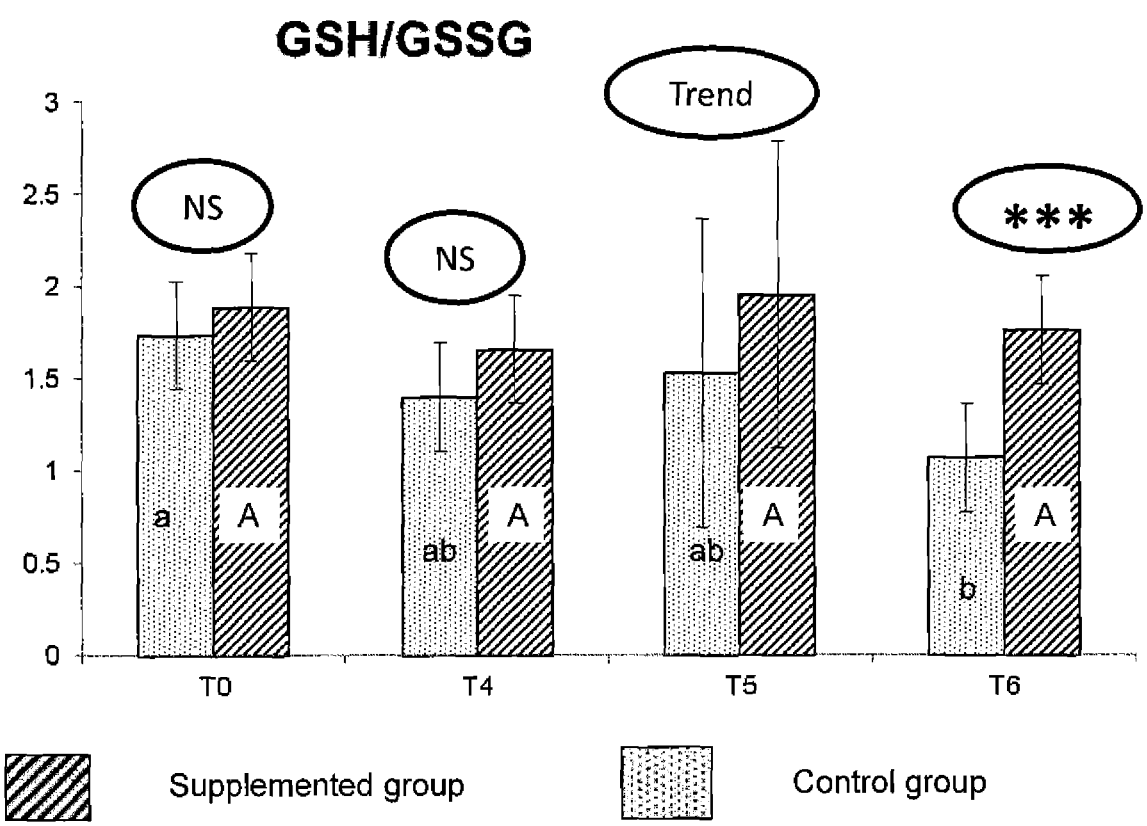

FIG. 4: shows the results obtained when assessing oxidative stress. FIG. 4a shows the results obtained when assessing Advanced Oxidative Protein product (AOPP). FIG. 4b shows the results obtained when assessing the ratio of reduced glutathione (GSH) to oxidized glutathione (GSSH). In FIGS. 4a and b, the letters in lower case are used to assess the effect of check point (time) for the control group (within group comparison). Upper case letters are used to assess the effect of check point (time) for the supplemented group (between group comparison). Different letters show significant difference at 5%.

Figure 5A:
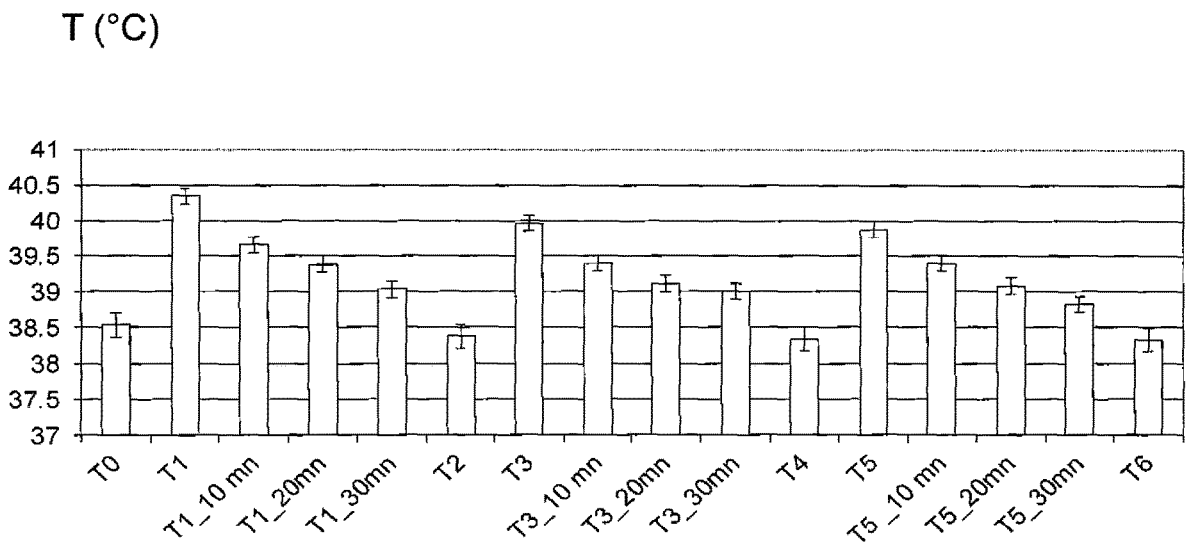
Figure 5B:
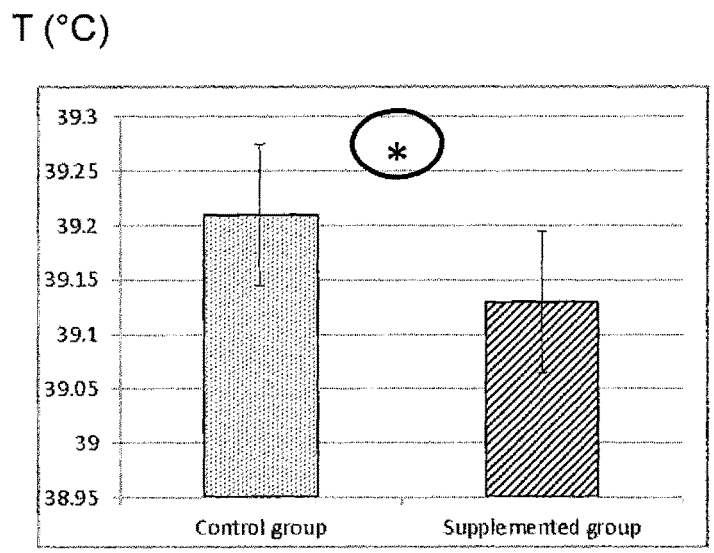

FIG. 5: shows the results of internal body temperature of control (C) and supplemented (S) groups. FIG. 5a shows the results of the body temperature at each interval in the trial. FIG. 5b shows the mean average results of body temperature between the control (C) and supplemented (S) groups.

EXAMPLE

Ten dogs belonging to the French army were used in the trial. All dogs were fed with the same diet (Profane®); comprising 33% crude protein, 22% crude fat, 2.5% fiber, 10% moisture, 7% ash, 1.6% calcium, 1.2% phosphorus plus Vitamins A, D3, E, Copper, Zinc and Selenium, Omega 3 and B. Total Metabolized energy=4,379 kcal/kg.

All dogs had the same body score, were homogenous in age (2 to 5 years) and were trained the same way for at least two months.

Each exercise consisted of 5 intensive sprints of 100 meters, 20 minutes of endurance running at 20 km/h and 5 intensive sprints of 100 meters.

The intensive stamina test is composed of resistance and endurance exercises:
  going in front of the dog for 50 meters and coming back
    to the handler after grabbing a tool by an assistant man,
    repeated five times while being timed;
  running for 20 minutes at constant speed (20 km/h);
  going in front of the dog for 50 meters and coming back
    to the handler after grabbing a tool by an assistant man,
    repeated five times while being timed.

Dogs performed the stamina test three times within a day with one hour of rest between each session. All dogs perform the trial twice (once as control (C) and once as supplemented (S) separately at least for 15 days so that each dog was its own control.

Unlimited water was provided before the exercise and during the recovery period. A standardized quantity of water was provided taking into account the weight of the dog at the time of administration of the placebo or the supplement.

The ten dogs were divided in two groups to allow a cross-over design (each dog was its own control):
  A: dogs from this group did not eat the supplement (C);
  B: dogs from this group ate the supplement (S).

A supplement was fed to the dogs after each exercise at T1, T3 and T5; see FIG. 2.

The dogs in group A were fed 150 ml of water as a placebo (control).

The supplement fed to the dogs in group B consisted of the following powder, instantaneously dissolved in 150 ml of water:
  75% of maltodextrin (IT 18) at 1.5 g of maltodextrin/kg
    of dog;
  25% of feather hydrolysate (Protamine, BCF) at 0.5 g of
    feather meal/kg of dog;
  Mixed in 150 ml of water.

Statistical Analysis

Data were analyzed using the mixed procedure of SAS version 9.3 software (SAS Institute Inc., Cary, N.C., USA). The fixed effects were: group effect in 2 levels (supplemented/control), check point effect either in 16 levels for physiological parameters (T0, T1, T1+10 min, T1+20 min, T1+30 min, T2, T3, T3+10 min, T3+20 min, T3+30 min, T4, T5, T5+10 min, T5+20 min, T5+30 min, T6) or in 4 levels for blood parameters (T0, T4, T5, T6) and the interaction Group effect×Check point effect. Sprinting time was added as a covariate in the statistical model to adjust the analysis to sprinting performance. Specifically for Interleukin 10 analysis, the value of interleukin 10 within group at T0 was added as covariate.

Dog was defined as a random term to fit with the cross over design (data pairment). According to the distribution of residuals of the statistical model, variables were previously logarithmic transformed (Interleukin 6 parameter) or not and ranked (creatine kinase parameter) or not. Level of significance was set at 5%. A trend noticed T in the graphs defined a P-value between 5 and 10%. One star "*" in the graphs defined a P-value between 1 and 5% (significant effect). Two stars "" in the graphs defined a P-value between 1 and 0.1% (very significant effect). Three stars"*" in the graphs defined a P-value between under 0.1% (highly significant effect).

Results

Four blood samples were performed to see the effect on inflammation, oxidative stress and muscle damage: before the first exercise (T0), before the last exercise (T4: encompassing the 2 first exercises), at this end of the last exercise (T5) and one hour after the end of the last exercise (T6).

Blood samples to measure lactates, CKmm, inflammatory, oxidative stress, and biochemistry parameters was performed at the beginning of the test (T0), before and just after the third exercise (T4 and T5), and 1 hour after the last exercise (T6).

| Parameters studied | Biological measured |
| --- | --- |
| Physiological parameters | Heart and respiratory frequencies [data not shown], body temperature. |
| Biochemical markers | Urea, creatinine, total protein, glucose, triglycerides, Na+, K+, lactate, albumin. [data not shown] |

-continued

| Parameters studied | Biological measured |
|---|---|
| Muscular damage marker | Creatine Kinase, Pro-Bnp |
| Inflammatory markers | MPO, cytokines (IL6, IL10, TNFα) |
| Oxidative stress marker | AOPP, GSH/GSSG, MPO |

Physiological parameters were measured before all exercises periods, and for 30 minutes after the end of exercises (just after, 10 minutes after, 20 minutes after, and 30 minutes after).

Muscle Damage

The results show that supplementation reduced muscle damage measured with several markers.

Pro-BNP is a marker of heart cell stress and more globally of muscle damage. Supplementation tends to decrease this marker level whatever the check point considered ($P=0.054$). This can be seen in FIG. 2a.

Creatine kinase is released into the blood when tissue is damaged due to cell lysis and therefore indicative of muscle cell stress. Supplementation significantly decreases this marker level especially after the two first exercises (T4; $P=0.002$), and at the end of the third exercise (T5; $P=0.022$). One hour the last exercise the difference between groups tend to remain in favour of supplementation ($P=0.09$). This can be seen in FIG. 2b.

Inflammation

The results show that supplementation reduced inflammation.

C Reactive Protein (CRP) is a marker indicative of inflammation. Supplementation highly decreases this marker level at the end of each exercise ($P<0.001$). CRP in the supplemented group was reduced by 50.25% compared to the control group whatever the check point considered (no significant interaction between group and check point effects). This is shown in FIG. 3a.

Myeloperoxydase (MPO) is a marker indicative of inflammation and oxidative stress. Supplementation reduces very significantly inflammation and oxidative stress after the 2 first exercises (T4) compared to control group and reduces highly significantly inflammation and oxidative stress after the last exercise (T5) and one hour after the last exercise (T6) compared to control group. Although inflammation increases at the end of the third exercise compared to basal state in the control group, the inflammation level stays at the basal level for the supplemented group. This is shown in FIG. 3b.

TNFα is a pro-inflammatory cytokine produced by T cells and macrophages during the inflammation process. Supplementation significantly reduces inflammation one hour after the last exercise compared to control. This is show in FIG. 3c.

IL6 is a pro-inflammatory interleukin produced by T cells and macrophages during the inflammation process. It is also a myokine: a cytokine produced by muscle during contraction. Moreover, in a human it has been shown that depletion in glycogen storage is linked with an increase in IL6 level. Supplementation significantly reduced IL6 level (Inflammation) one hour after the last exercise compared to control. This is indicative of reducing inflammation, as well as reducing depletion in glycogen storage in the muscles. This is shown in FIG. 3d.

IL10 is an interleukin produced during inflammation. Supplementation highly significantly reduces IL10 level at the end of the last exercise ($P<0.001$) and one hour after the last exercise ($P<0.001$), indicative of reducing inflammation. This is shown in FIG. 3e.

Oxidative Stress

The results show that supplementation educed oxidative stress.

Advance Oxidation Protein Product (AOPP) is a marker of protein oxidation (a type of oxidative stress). Supplementation very significantly reduces AOPP level at the end of the last exercise and highly significantly reduces AOPP level one hour after the last exercise compared to control, indicative of reducing oxidative stress. This is shown in FIG. 4a.

A decrease of the ratio of reduced glutathione (GSH) to oxidized glutathione (GSSG) is considered indicative of oxidative stress. Supplementation highly significantly increases the ratio of GSH/GSSH at the end of the last exercise and one hour after the last exercise, indicative of reducing oxidative stress. This is shown in FIG. 4b.

Temperature

A significant reduction of temperature during exercise is also observed with the group of dogs which were fed the supplement. Indeed the supplementation permits body temperature to decrease by 0.2% during exercises, this is statistically significant. This is shown in FIG. 5.

CONCLUSION/DISCUSSION

The results showed that supplementing a dog with the foodstuff of the present invention after each exercise improved their subsequent performance and improved their recovery after each exercise. Biomarkers relating to muscle damage, inflammation and oxidative stress in the blood samples taken from the dogs supplemented with the composition of the present invention were shown to be reduced compared to dogs not supplemented after exercising. In addition, it was shown that the body temperature of the dogs was also reduced.

What is claimed is:

1. A post-exercise, performance-enhancing foodstuff consisting of:
   10-50% of feather hydrolysate on a dry matter basis,
   50-90% of one or more hydrolysed carbohydrates on a dry matter basis; and optionally, liquid;
   wherein the ratio of feather hydrolysate to hydrolysed carbohydrate is from 1:1 to 1:9 and the hydrolysed carbohydrate consists of dextrose, maltodextrin, or a combination thereof.

2. The post-exercise, performance-enhancing foodstuff of claim 1, wherein the hydrolysed carbohydrate is a combination of maltodextrin and dextrose, or maltodextrin alone.

3. The post-exercise, performance-enhancing foodstuff of claim 1, wherein the ratio of feather hydrolysate to hydrolysed carbohydrate is from about 1:3 to 1:4.

4. The post-exercise, performance-enhancing foodstuff of claim 1, which is a wet product, dry product, semi-moist product or a liquid.

5. The post-exercise, performance-enhancing foodstuff of claim 1, wherein the feather hydrolysate is produced by hydrolyzing poultry feathers.

6. The post-exercise, performance-enhancing foodstuff of claim 1, where in the feather hydrolysate is in the form of a powder.

7. The post-exercise, performance-enhancing foodstuff of claim 1, consisting of 15-25% of feather hydrolysate on a dry matter basis.

8. The post-exercise, performance-enhancing foodstuff of claim 1, consisting of 60-80% of one or more hydrolysed carbohydrates on a dry matter basis.

* * * * *